United States Patent
Nielsen (10) Patent No.: US 11,033,202 B2
(45) Date of Patent: Jun. 15, 2021

(54) METHOD TO DETERMINE INDICES OF VENTILATION INHOMOGENEITY E.G. LUNG CLEARANCE INDEX (LCI) OF A PAEDIATRIC TEST SUBJECT

(71) Applicant: Pulmotrace ApS, Glamsbjerg (DK)

(72) Inventor: Jørgen G. Nielsen, Aarup (DK)

(73) Assignee: PULMOTRACE APS, Glamsbjerg (DK)

( * ) Notice: Subject to any disclaimer, the term of this patent is extended or adjusted under 35 U.S.C. 154(b) by 486 days.

(21) Appl. No.: 15/159,027

(22) Filed: May 19, 2016

(65) Prior Publication Data

US 2016/0345861 A1    Dec. 1, 2016

(30) Foreign Application Priority Data

May 26, 2015   (EP) .................................... 15169163

(51) Int. Cl.
*A61B 5/08*     (2006.01)
*A61B 5/093*    (2006.01)
(Continued)

(52) U.S. Cl.
CPC ............ *A61B 5/0813* (2013.01); *A61B 5/082* (2013.01); *A61B 5/087* (2013.01); *A61B 5/093* (2013.01); *A61B 5/097* (2013.01); *A61B 2503/04* (2013.01)

(58) Field of Classification Search
None
See application file for complete search history.

(56) References Cited

U.S. PATENT DOCUMENTS

2011/0098589 A1* 4/2011 Clemensen .......... A61B 5/0813
                                                          600/532

FOREIGN PATENT DOCUMENTS

EP    2 311 371 A1    4/2011

OTHER PUBLICATIONS

Morris; The open circuit nitrogen washout technique for measuring the lung volume in infants: methodological aspects; Thorax 1999;54:790-795.*

(Continued)

*Primary Examiner* — Kaylee R Wilson
*Assistant Examiner* — Jay B Shah
(74) *Attorney, Agent, or Firm* — Brinks Gilson & Lione; John C. Freeman (57) ABSTRACT

Methods and systems to determine the lung clearance index (LCI) or other indices of ventilation inhomogeneity of lungs of a paediatric subject are provided. Inert tracer gas is washed-in and the wash-out is conducted by inhaling atmospheric air from the surroundings and exhaling to a confined space until the end-tidal tracer gas concentration has fallen below a predetermined fraction of the starting concentration. The LCI is calculated as the ratio between the cumulative expired volume ($V_{CE}$) required to clear the inert tracer gas concentration from the lungs below a predetermined fraction of the starting concentration and the functional residual capacity (FRC) determined by dividing the net volume of inert tracer gas exhaled with the difference in end-tidal fractional concentration of the inert tracer gas at the start and end of the wash-out period; where $V_{CE}$ is determined by measuring the total volume in the collection bag after completed wash-out period.

16 Claims, 8 Drawing Sheets

(51) Int. Cl.
*A61B 5/097* (2006.01)
*A61B 5/087* (2006.01)

(56) References Cited

OTHER PUBLICATIONS

Jonmarker et al.; Measurment of FRC by SF6 Washout; Anesthediology; 63:89-95; 1985.*
Innocor—Lung Clearance Index Method Issue A, Rev 3. 2013 (Year: 2013).*
Johnson et al.—Cardiac output during exercise by the open circuit acetylene washin method: comparison with direct Fick; J Appl Physiol 88: 1650-1658, 2000 (Year: 2000).*
Culver—Pulmonary Function Testing, Measurement by Nitrogen Washout—Clinical Respiratory Medicine (Fourth Edition), 2012 (Year: 2012).*
Gustafsson, P.M. et al.; "Evaluation of ventilation maldistribution as an early indicator of lung disease in children with cystic fibrosis"; European Respiratory Journal, vol. 22; Dec. 2003; pp. 972-979.
Hoo, A. et al.; Lung function is abnormal in 3-month-old infants with cystic fibrosis diagnosed by newborn screening; Thorax; Jun. 29, 2012; 8 pages.
Lum, S. et al.; "Early detection of cystic fibrosis lung disease: multiple-breath washout versus raised volume tests"; Thorax; Nov. 22, 2006; pp. 341-347.

* cited by examiner

METHOD TO DETERMINE INDICES OF VENTILATION INHOMOGENEITY E.G. LUNG CLEARANCE INDEX (LCI) OF A PAEDIATRIC TEST SUBJECT

RELATED APPLICATIONS

This application claims the benefit of EP 15169163.1, filed May 26, 2015, which is hereby incorporated by reference in its entirety.

BACKGROUND OF THE INVENTION

1. Field of the Invention

The present invention relates to a method to determine the lung clearance index (LCI) or other indices of ventilation inhomogeneity of the lungs of a paediatric test subject. Wash-in is used to wash-in the inert tracer gas and the wash-out is conducted by inhaling atmospheric air from the surroundings and exhaling to a confined space until the end-tidal tracer gas concentration has fallen below a predetermined fraction of the starting concentration. The LCI of a paediatric test subject is calculated as the ratio between the cumulative expired volume ($V_{CE}$) required to clear the inert tracer gas concentration from the lungs of the paediatric test subject below a predetermined fraction of the starting concentration and the functional residual capacity (FRC) where FRC is determined by dividing the net volume of inert tracer gas exhaled by said paediatric test subject with the difference in end-tidal fractional concentration of the inert tracer gas at the start and end of the wash-out period; and where $V_{CE}$ is determined by measuring the total volume in the collection bag after completed wash-out period.

2. Background

Spirometry, i.e. the measurement of inspired and expired air flows and volumes at the airway opening of a test subject, is the commonest means of assessing lung function. Diseases causing obstruction of larger airways will eventually result in reduced expiratory flows and volumes as measured by spirometry. However, spirometry findings are often normal in the early stages of peripheral airway diseases, and therefore changes in the peripheral airways associated with early cystic fibrosis (CF) disease, early chronic obstructive pulmonary disease or mild asthma cannot be detected by spirometry until the disease has progressed considerably because the small airways only contribute to a very limited extent to the total airway resistance.

Peripheral airway diseases do, however, affect the way air mixes within the lungs and thus lead to increased ventilation inhomogeneity.

Ventilation inhomogeneity may be assessed using the multiple-breath wash-out (MBW) test performed by washing out either a resident gas (e.g. nitrogen) from the lungs using e.g. pure oxygen or a previously washed-in non-resident inert tracer gas during tidal breathing of room air. When using the MBW method to assess ventilation distribution in the lungs, several indices of overall ventilation inhomogeneity can be calculated as sensitive tracers of airway disease. They all reflect differences in specific ventilation between large and/or relatively small lung regions, resulting in delayed wash-out of the tracer gas from the poorly ventilated regions. Examples of indices of overall ventilation inhomogeneity that can be calculated from the MBW are mixing ratio (MR), which is calculated as the ratio between the actual and the estimated ideal number of breaths needed to lower the end-tidal tracer gas concentration to a certain fraction of the starting value, moment ratios of the wash-out curve and lung clearance index (LCI). The LCI can be calculated as the cumulative expired volume ($V_{CE}$) required to clear the gas from the lungs minus the number of wash-out breaths multiplied by external dead space outside the lips, divided by the subject's FRC (up to the lips). FRC is the amount of air that stays in the lungs after a normal expiration. In other words, LCI represents the number of lung volume turnovers (i.e. FRCs) that the subject must breathe to clear the lungs from the tracer gas (by convention, to an end-tidal concentration of 1/40th of the starting concentration over three subsequent breaths). Disregarding the correction for external dead space the equation is:

$$LCI = \frac{V_{CE}}{FRC}$$

The LCI is simple to calculate and intuitively understandable, and it is questionable whether any other index is more sensitive, reliable and clinically useful.

For the MBW test using a non-resident inert tracer gas there are several different gases with low solubility in blood and tissues that can be used, including helium (He) and sulfur hexafluoride ($SF_6$). Normally, a respiratory mass spectrometer is used for the gas analysis, and a flowmeter, e.g. a pneumotachometer, is used to record the inspiratory and expiratory flows at the mouth. The pressure gradient measured is directly related to flow thus allowing a computer to derive a flow-curve measured in L/minute. The test subject is breathing through a mouthpiece or a face mask connected to the flowmeter, and a gas sampling tube is connected to the breathing assembly for sidestream gas analysis. When performing MBW tests by use of a non-resident tracer gas, the tracer gas must first be washed in to obtain an even concentration in the lungs before the wash-out can start.

A conventional breath-by-breath system for inert gas wash-out further consists of a unit for delivering the wash-in gas mixture. This can be achieved by use of a bias flow of the gas mixture. A sufficiently long wash-in period is needed to allow the tracer gas to fully equilibrate in the lungs.

The wash-out phase is initiated by disconnecting the bias flow during expiration. The wash-out should continue until the end-tidal tracer gas concentration has fallen below 1/40th of the starting concentration over three successive breaths.

Guidelines on lung function testing recommend that the MBW test be repeated in order to obtain at least two tests in which the difference between two FRC values is less than 10% when comparing the higher to the lower FRC value.

In the conventional MBW test the FRC is calculated from the net volume of inert gas exhaled divided by the difference in end-tidal fractional concentration at the start and end of the wash-out:

$$FRC = \frac{\text{Net volume of inert gas exhaled}}{C_{ET,start} - C_{ET,end}}$$

As the net volume of inert gas exhaled (numerator) is obtained by integration of the product of respiratory flow and fractional tracer gas concentration (i.e. expired and re-inspired tracer gas volumes on a breath-by-breath basis), accurate determination of the FRC requires a rapid dynamic response and data acquisition rate of the gas analyser. Proper alignment in time of the respiratory flow signal and fractional tracer gas concentration prior to the calculation is also critical. This makes demands on the performance of the gas analyser and the calibration of the equipment.

In adults the above described method works but in children several problem can arise, especially in small children and in newborns. It has previously successfully been shown that Multiple breath washout testing (MBW) can be used in infants to assess lung clearance index (LCI), (Lum S, Gustafsson P, Ljungberg H, Hulskamp G, Bush A, Carr S B, et al. Early detection of cystic fibrosis lung disease: multiple-breath washout versus raised volume tests. Thorax. 62(4):341-7, Hoo A F, Thia L P, Nguyen T T, Bush A, Chudleigh J, Lum S, et al. Lung function is abnormal in 3-month-old infants with cystic fibrosis diagnosed by newborn screening. Thorax. 67(10):874-81). In addition, the value of LCI is well recognised in children and adults. It has been shown to be elevated as early as 3 months of age in infants with CF (Hoo A F, Thia L P, Nguyen T T, Bush A, Chudleigh J, Lum S, et al. Lung function is abnormal in 3-month-old infants with cystic fibrosis diagnosed by newborn screening. Thorax. 67(10):874-81).

Lung function test of paediatrics, especially small children and newborns, is a very challenging area, but lung function tests have the potential to be an important tool for monitoring Cystic Fibroses (CF) and for screening newborns for CF.

The U.S. food and drug administration categorizes pediatric subpopulation according to the following age ranges. The newborn population range from birth to 1 month of age. The infant population range from 1 month to 2 years of age. The child population range from 2 years to 12 years of age. The adolescent population range from 12 to 21 years of age. The European Medicines Agency categorizes paediatric medicines according to the following populations. The newborn population includes pre-term to term and up to 28 days. The infant population are from 1 month to 23 months. The child population are form 2 years to 11 years. Adolescents are from 12 years to 18 years.

When paediatric, especially small children and newborns, inhale and breathe pure oxygen it can alter the breathing pattern which will invalidate the test results of the MBW test.

In paediatric, especially in small children and newborns, both the response time and the dead space are subjects to challenges in a conventional MBW method, which have resulted in that the method is not used for this group of patients. By the described conventional measuring setup, the dead space will be at least of the same size as the volume of the flowmeter. In adults this is not much of a problem since the dead space volume is small compared to the physiologic dead space. But this is not the case with pediatric subjects, where the extra volume induced by the flowmeter will result in a very large dead space volume. Small children and newborns have fast respiratory rates and smaller lung volumes than adults. One could improve the response time characteristic by increasing the gas flow to the gas analyser but this would not work in tests of in small children and newborns since the gas flow will influence the breathing flow.

So since accurate flow and gas signal measurement becomes increasingly challenging at fast respiratory rates and smaller lung and tidal volumes, it renders the existing MBW test setup practically impossible to use in the paediatric patient group. Therefore a method and a system for measuring indices of ventilation inhomogeneity e.g. lung clearance index (LCI) of a paediatric test subject is needed.

SUMMARY OF THE INVENTION

One object of the present invention is to provide a method to avoid the main problems in the determination of the lung clearance index of a paediatric test subject.

This is accomplished by using a method to determine the lung clearance index (LCI) of a paediatric test subject, said method comprising the steps of: wash-in of an inert tracer gas until a constant concentration of the inert tracer gas in the lungs of the paediatric test subject is reached; washout of the inert tracer gas from the lungs of the paediatric test subject during a washout period until the end-tidal tracer gas concentration has fallen below a predetermined fraction of the concentration in the beginning of the wash-out period by inhaling atmospheric air from the surroundings and exhaling to a confined space; wherein the lung clearance index (LCI) is determined in steps of: determining the net volume of inert tracer gas exhaled by said paediatric test subject by measuring the concentration of the inert tracer gas in the confined space after completed wash-out period and measuring the total cumulative expired volume (VCE) in the confined space after completed wash-out period, where the total cumulative expired volume (VCE) is the volume required to clear the inert tracer gas concentration from the lungs of the paediatric test subject below the predetermined fraction of the concentration in the beginning of the wash-out period; determining the functional residual capacity (FRC) by dividing the net volume of inert tracer gas exhaled by said paediatric test subject with the difference in end-tidal fractional concentration of the inert tracer gas at the start and end of the wash-out period; calculation of the LCI as the ratio between VCE and FRC.

In one embodiment the method uses open circuit wash-in of the inert tracer gas. By open circuit is meant that the paediatric test subject inhale the inert tracer gas from a reservoir to wash-in the inert tracer gas whilst expiring into room air.

In another embodiment the method uses bias flow of the inert tracer gas to wash-in the inert tracer gas.

In another embodiment the method uses rebreathing of the inert tracer gas to wash-in the inert tracer gas. Rebreathing is a closed system where the paediatric test subject inhale and exhale the inert tracer gas from and to a reservoir.

To perform a multiple-breath inert gas wash-in/wash-out test according to the method, the paediatric test subject is connected to means for washing in the inert tracer gas via a valve assembly. In a preferred embodiment of the invention the means are an inhalation bag (also called a wash-in bag in the present invention). The test subject inspires the inert tracer gas from the flow-past via the valve assembly.

In one embodiment the non-rebreathing valve assembly is constructed by one-way valves allowing gas to flow in one direction only. Because of the construction of the valve, the test subject does not breathe the non-resident inert tracer gas back to the inhalation bag during exhalation. Instead the test subject expires to the surrounding air.

The test subject preferably uses a face mask instead of nose clip and mouthpiece. However, if the paediatric test subject is a child or adolescent a nose clip and mouthpiece can be used.

The test subject inspires the inert tracer gas via the valve assembly and exhales (e.g. to the surrounding air) a number of times until the inert tracer gas is well mixed in the lungs and when the concentration of the tracer gas is constant e.g. below a predetermined threshold fluctuation the first time period called wash-in, is over. The wash-in period is followed by a period where the test subject is inhaling fresh air from the surrounding and exhale to a confined space (e.g. a bag) that collects all the expired air from the test subject (wash-out period). The confined space collect the expirate. In one embodiment the confined space is a bag and is called a collection bag or a washout bag. The concentration of the inert tracer gas is monitored until the concentration has reached a predetermined fraction (e.g. 1/40) of the concentration in the beginning of the wash-out period.

So, during the testing (both during the wash-in and the wash-out period) the concentration in the inhaled and/or exhaled air at the end of each breath of the inert gas in the mixture is measured by a fast responding gas analyser. Instead of gas concentration the gas analyser may equally well measure the partial pressure of the gas. The partial pressure can be obtained from the fractional concentration of dry gas or any other measure of gas concentration or pressure using appropriate conversion factors as known in the art.

The method allows the paediatric test subject to breathe in the wash-in inert gas whilst expiring into room air. Once the wash-in period is deemed complete, the circuit is automatically or manually changed to allow the paediatric test subject to breathe in room air, whilst the expired inert tracer gas is collected in the confined space.

By the above method is achieved that LCI of a paediatric test subject can be calculated without directly measuring flow since FRC is derived from the volume of expired inert tracer gas, and cumulative expired volume from the volume of the confined space. This enables a small dead space of the setup (little more than the mask) since a flowmeter can be omitted from the setup and it removes the difficulty of integrating flow and gas signals at fast respiratory rates. Also, the method achieves the advantage that only end-tidal measurement of the inert gas is required whereas measurement of intra breath concentration profile is unnecessary. This substantially reduces the response time requirements to the gas analyser.

The method for performing MBW in paediatric test subjects is highly accurate as shown in a realistic infant lung simulation at BTPS conditions (in respiratory physiology lung volumes and flows are standardized to barometric pressure at sea level, body temperature, saturated with water vapour: body temperature and pressure, saturated). The accuracy of the method is superior to that of previously described systems at higher FRC's and is within the standards set by international guidelines. The method is capable of highly accurate measurement of FRC at volumes down to 100 ml as shown in the lung simulation.

In one embodiment the inert tracer gas is comprised in a gas mixture.

In one embodiment of the method the inert tracer gas is a gas with a negligible solubility in blood and tissue.

The inert tracer gas can be one of: $SF_6$ or He or any other gas with similar solubility in blood and without physiological effects on the test subject.

In one embodiment of the method the inert tracer gas is $SF_6$.

In one embodiment the method uses an oxygen enriched gas mixture comprising the inert tracer gas to avoid oxygen deficiency during the manoeuvre.

In one embodiment of the method the determination of the gas concentration is performed by at least one sensitive gas analyser e.g. based on photoacoustic spectroscopy (PAS) or a mass spectrometer.

In one embodiment the method is combined with a sensitive $SF_6$ analyser. A PAS analyser exists which has a unique sensitivity to $SF_6$ and is able to measure $SF_6$ accurately in the range 0-0.05% during wash-out. A typical concentration used in the inspired gas mixture for open-circuit wash-in when applying mass spectrometry for gas analysis is 4%. Thus, comparing open circuit multiple-breath wash-in using e.g. 0.2% $SF_6$ as the initial concentration in the bag and open-circuit multiple-breath wash-in using 4% $SF_6$ in the inspired gas mixture have the effect that a 20 times lower concentration of $SF_6$ can be used.

LCI represents the number of lung volume turnovers (i.e. FRCs) that the subject must breathe to clear the lungs from the tracer gas (by convention, to an end-tidal concentration of 1/40th of the starting concentration over three subsequent breaths). Disregarding the correction for external dead space the equation is:

$$LCI = \frac{V_{CE}}{FRC}$$

In the present method, the concentration of the inert tracer gas is monitored and when the concentration is constant (below a predetermined threshold value regarding the fluctuation of the concentration), the first time period called wash-in is over. Hereafter the wash-out period begins where the concentration of the inert tracer gas is monitored at the end of each breath until the concentration has reached 1/40 of the concentration in the beginning of the wash-out period. It is not necessary to continuous monitor the instantaneous concentration during the whole breathing cycle since the net volume of inert tracer gas exhaled, in the present invention, is determined by measuring the concentration of the inert tracer gas in the confined space (e.g. in the collection bag) after completed wash-out and measuring the total volume in the confined space after completed wash-out.

The net volume of inert tracer gas exhaled and the difference in end-tidal fractional concentration of the inert tracer gas at the start (in the below equation $SF6_{init}$) and end (in the below equation $SF6_{end}$) of the wash-out is used for accurate determination of the functional residual capacity (FRC) which in the present invention is calculated according to the equation below:

$$FRC = \frac{SF6_{exp}}{SF6_{init} - SF6_{end}} \cdot V_{bag} \ (ATPS)$$

Where $V_{bag}$ is calculated as below:

$$V_{bag} = T_{empty} \cdot Fill_{flow} \quad (ATPS)$$

And where $VCE = V_{bag}$ (ATPS)

Where $T_{empty}$: Time to empty bag in seconds $Fill_{flow}$: Calibrated filling flow (=emptying flow) in l/s $SF6_{exp}$: Mean gas concentration of inert tracer gas in the collection bag $SF6_{init}$: Gas concentration of inert tracer gas at the start of washout $SF6_{end}$: End tidal gas concentration of inert tracer gas at the end of washout The multiple-breath wash-out (MBW) is used for determination of the cumulative expired volume ($V_{CE}$) required to clear the inert tracer gas from the lungs. $V_{CE}$ is in the present invention determined by measuring the total volume in the collection bag (confined space) after completed wash-out.

In the interest of brevity dead spaces on each side of the valve are not accounted for, but these can easily be incorporated.

All mathematical expressions and illustrations throughout this document are made using fractional concentrations of dry inert gas. Fractional concentrations can be replaced by partial pressures using appropriate conversion factors as known in the art.

Volumes can be expressed at different gas conditions using appropriate conversion factors as known in the art.

The present method is more robust than the traditional wash-out technique for determination of FRC, because it is independent of the critical time alignment between gas analyser and flowmeter signals. Further, it relaxes the requirements to rise time of the gas analyser because only end-tidal concentrations are needed in determining the gas dilution, whereas in the conventional open-circuit method a short rise time and accurate time alignment prior to integrating the product of flow and gas concentration signals are important in order to obtain accurate values of the flux of $SF_6$ in the rapid transitions during the beginning of expiration (phase II of the breath) and inspiration.

According to another aspect, the present invention also relates to a system adapted to determine the lung clearance index (LCI) of the lungs of a paediatric test subject, said system comprising; a valve assembly setup comprising: means for said paediatric test subject to inhale an inert tracer gas mixture comprising an inert tracer gas; a confined space for said paediatric test subject to exhale to for collection of the exhaled volume of air by said paediatric test subject during a wash-out period, said volume comprising the inert tracer gas; at least one gas analyser for obtaining the fractional concentration at the end of each breath of said inert tracer gas inhaled and exhaled by said paediatric test subject until the concentration has reached a predetermined fraction of the concentration in the beginning of the wash-out period; processing means for determining the LCI of the lungs of the paediatric test subject by using the net volume of inert tracer gas exhaled by said paediatric test subject during the wash-out period, said net volume of inert tracer gas exhaled is obtained by measuring the concentration of the inert tracer gas in the confined space after completed wash-out period and measuring the total cumulative expired volume ($V_{CE}$) in the confined space after completed wash-out period, where the total cumulative expired volume ($V_{CE}$) is the volume required to clear the inert tracer gas concentration from the lungs of the paediatric test subject below the predetermined fraction of the concentration in the beginning of the wash-out period; determining the functional residual capacity (FRC) by dividing the net volume of inert tracer gas exhaled by said paediatric test subject during the wash-out period with the difference in end-tidal fractional concentration of the inert tracer gas at the start and end of the wash-out period; where LCI is determined as the ratio between $V_{CE}$ and FRC.

Hereby a system can be constructed that can achieve the same advantages as described above.

In one embodiment the system uses open circuit wash-in of the inert tracer gas. By open circuit is meant that the paediatric test subject inhale the inert tracer gas from a reservoir to wash-in the inert tracer gas whilst expiring into room air.

In another embodiment the system uses bias flow of the inert tracer gas to wash-in the inert tracer gas.

In another embodiment the system uses rebreathing of the inert tracer gas to wash-in the inert tracer gas. Rebreathing is a closed system where the paediatric test subject inhale and exhale the inert tracer gas from and to a reservoir.

The valve assembly is preferably a one way valve assembly.

In a preferred embodiment of the invention the means are an inhalation bag (also called a wash-in bag in the present invention).

In one embodiment the system can be described as an open-closed circuit system comprising a one way valve assembly comprising a inhalation bag containing the inert tracer gas to be washed-in in the lungs of the test subject and a bag to collect the expired washed-out inert tracer gas. The one way valve assembly comprises a series of pneumatic valves and the test subject (the patient) is connected to the system by a facemask. This open-closed circuit system allows the paediatric subject e.g. an infant or newborn to breathe in the inert tracer gas whilst expiring into room air during the wash-in period. Once wash-in is deemed complete, the circuit is automatically or manually changed to allow the paediatric subject to breathe in room air, whilst the expired inert tracer gas is collected in a bag.

In one embodiment of the system the inert tracer gas is a gas with a negligible solubility in blood and tissue.

In one embodiment the system uses a gas mixture containing the inert tracer gas, $SF_6$, which has very low solubility in blood and tissues and which is a good choice when using infrared gas analysis techniques.

In one embodiment the system uses an oxygen enriched gas mixture comprising the inert tracer gas to avoid oxygen deficiency during the manoeuvre.

The gas analysers could be any apparatus suitable for obtaining the fractional concentration of the inert gas. Such apparatus could for instance be a mass spectrometer or an infrared photoacoustic multi-gas analyser, etc. In one embodiment of the invention the gas analysis is performed by a sensitive gas analyser with a high signal-to-noise ratio for example based on photoacoustic spectroscopy (PAS). The gas analysers can measure the end-tidal partial pressures or concentrations or a continuous partial pressure or concentration curve of the inert tracer gas.

In one embodiment of the system the at least one sensitive gas analyser obtains the fractional concentration at the end of each breath of said inert tracer gas inhaled and exhaled by said paediatric test subject until the concentration has reached $\frac{1}{40}$th of the starting concentration in the beginning of the wash-out period.

In one embodiment the concentration of the inert tracer gas is measured throughout washout by a photoacoustic gas analyser. When end expired inert tracer gas reaches $<\frac{1}{40}^{th}$ of starting concentration, collection of expirate stops and the paediatric test subject is switched to room air. The total volume of expired air (including the inert tracer gas), and the inert tracer gas concentration of this, are then measured.

The accuracy of the system is superior to that of previously described systems at higher FRC's and is within the standards set by international guidelines. The system is capable of highly accurate measurement of FRC at volumes down to 100 ml as shown in the lung simulation.

In one embodiment the system comprises a cylinder for containing the inert tracer gas mixture. Since the system has incorporated a sensitive gas analyser with a high signal-to-noise ratio a smaller amount of inert gas is necessary for performing the test. The cylinder contains approx. 150 ml of pressurized inert gas mixture which corresponds to 18 l of inert gas mixture at ambient pressure. In normal open-circuit wash-in the gas cylinder contains e.g. 1500 l of inert gas or more. The high concentration of inert gas inside the gas cylinder means that approx. only $\frac{1}{10}^{th}$ of the inhaled gas comes from the cylinder, the rest is atmospheric air or oxygen. The system can in one embodiment also comprise means to dilute the inert tracer gas mixture with air or oxygen. By using this dilution principle a much more compact system is obtained.

The processing means for determining LCI of the lungs of a test subject is comprised in a control system of the system.

In one embodiment of the system, said processing means for determining LCI comprises processing means for determining the net volume of inert tracer gas exhaled by said paediatric test subject during the wash-out period, said net volume of inert tracer gas exhaled is obtained by measuring the concentration of the inert tracer gas in the collection bag (confined space) after completed wash-out period and measuring the total volume in the collection bag (confined space) after completed wash-out period, processing means for determining FRC by dividing the net volume of inert tracer gas exhaled by said paediatric test subject during the wash-out period with the difference in end-tidal fractional concentration of the inert tracer gas at the start and end of the wash-out period and processing means for determining $V_{CE}$ required to clear the inert tracer gas concentration from the lungs of the paediatric test subject below a predetermined fraction of the starting concentration by measuring the obtained total volume in the collection bag (confined space) after completed wash-out period. LCI is determined as the ratio between $V_{CE}$ and FRC. The processing means is comprised in the control system of the system.

In one embodiment of the system at least one gas analyser for obtaining the fractional concentration of said inert tracer gas inhaled and exhaled by said test subject comprises means for obtaining the partial pressure of said inert tracer gas.

In one embodiment of the system the valve assembly can switch (manually or automatically) between open circuit wash-in mode and wash-out mode.

In one embodiment the system comprises a gas dose facility enabling filling of the wash-in bag to a known volume with a gas mixture containing the inert tracer gas. Alternatively, the wash-in bag can be prepared manually.

According to another aspect, the present invention also relates to the use of the method according to the above to determine the lung clearance index (LCI) of a test subject.

According to another aspect, the present invention relates to a computer-readable medium having stored therein instructions for causing a processing unit to execute the above described method. Hereby the same advantages as described above are achieved.

The U.S. food and drug administration categorizes paediatric subpopulation according to the following age ranges. The newborn population range from birth to 1 month of age. The infant population range from 1 month to 2 years of age. The child population range from 2 years to 12 years of age. The adolescent population range from 12 to 21 years of age. The European Medicines Agency categorizes paediatric medicines according to the following populations. The newborn population includes pre-term to term and up to 28 days. The infant population are from 1 month to 23 months. The child population are form 2 years to 11 years. Adolescents are from 12 years to 18 years.

According to the present method, paediatric test subjects can be defined according to the U.S. food and drug administration or according to the European Medicines Agency as indicated above.

According to the present method, paediatric test subjects mean all of the above mentioned paediatric subpopulations.

In a preferred embodiment the paediatric test subjects are one of newborns, infants, child's, adolescent's.

In a preferred embodiment the paediatric test subjects are newborns. In a preferred embodiment the paediatric test subjects are infants. In a preferred embodiment the paediatric test subjects are child's. In a preferred embodiment the paediatric test subjects are adolescent's.

BRIEF DESCRIPTION OF THE DRAWINGS

In the following, preferred embodiments of the invention will be described referring to the figures, where.

DESCRIPTION OF PREFERRED EMBODIMENTS

Figure 1:
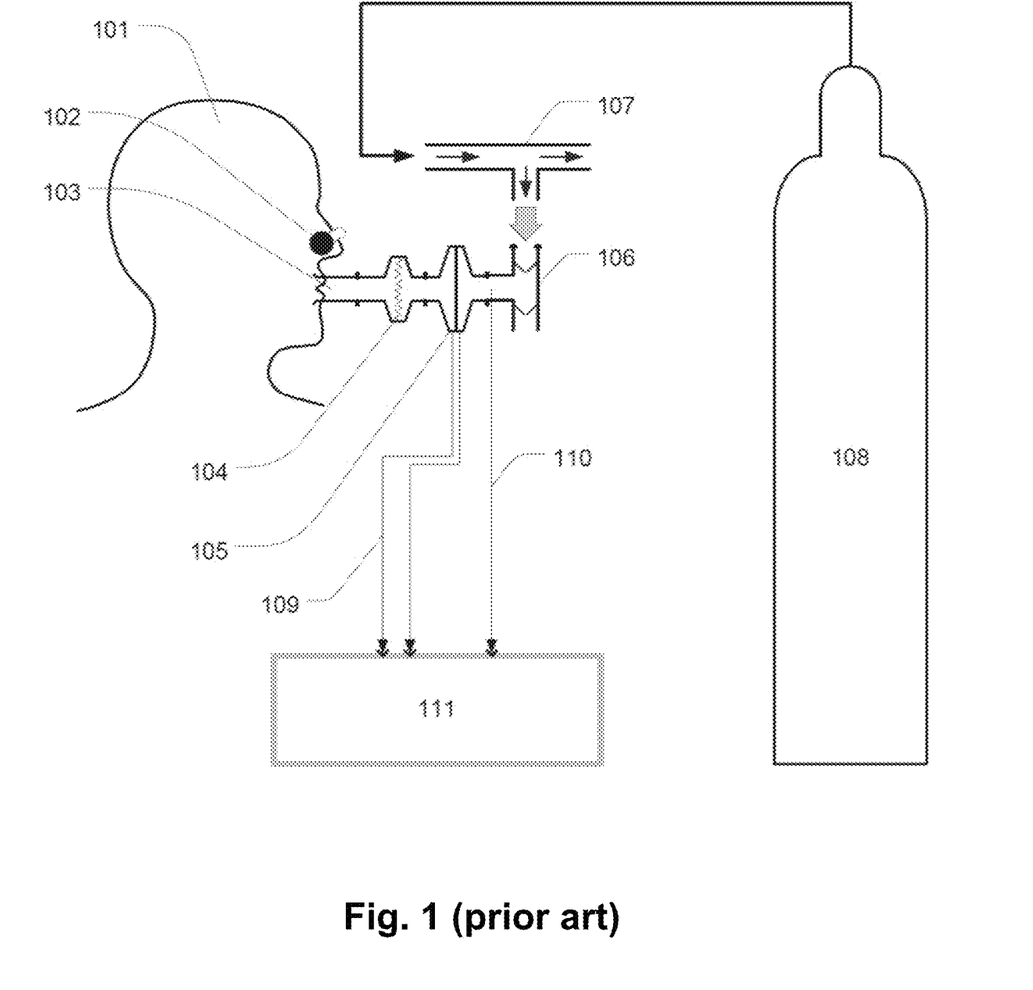
FIG. 1 (prior art) is a schematic diagram illustrating a conventional setup for multiple-breath inert gas wash-in/wash-out tests for determination of FRC and ventilation distribution (LCI) as known in the art.

FIG. 1 (prior art) is a schematic diagram illustrating a conventional setup for multiple-breath inert gas wash-in/wash-out tests for determination of FRC and ventilation distribution (LCI) as known in the art. The setup includes a bias flow of a mixture containing a non-resident inert tracer gas for wash-in in the flow past assembly 107. A test subject 101 having the nose occluded with a nose clip 102 breathes through a mouthpiece 103, a bacterial filter 104, a respiratory flowmeter 105 and a non-rebreathing valve assembly 106. The gas reservoir 108 is coupled to a flow past assembly 107 via a gas line. Flowmeter connection(s) 109 and a gas sample line 110 are also part of the setup.

To perform a multiple-breath inert gas wash-in/wash-out test, the test subject 101 inspires the non-resident inert tracer gas from the flow past assembly 107 through the non-rebreathing valve assembly 106. The non-rebreathing valve assembly 106 is constructed by one-way valves allowing gas to flow in one direction only. Because of the construction of the valve 106, the test subject does not breathe the non-resident inert tracer gas back to the flow past assembly 107 during exhalation. Instead the test subject expires to the surrounding air. The test subject 101 may use a face mask instead of nose clip 102 and mouthpiece 103. The analyser unit 111 consists of a measuring apparatus comprising flowmeter electronics and at least one gas analyser.

A typical test consists of a period where the test subject inspires from the flow past and exhales to the surrounding air a number of times until the concentration of the tracer gas is constant e.g. below a predetermined threshold fluctuation (wash-in period) followed by a period where the test subject is breathing fresh air (wash-out period). During the testing (both during the wash-in and the wash-out period) the concentration in the inhaled and/or exhaled air of the inert gas in the mixture is measured by a fast responding gas analyser. Instead of gas concentration the gas analyser may equally well measure the partial pressure of the gas. The partial pressure can be obtained from the fractional concentration of dry gas or any other measure of gas concentration or pressure using appropriate conversion factors as known in the art. Also the flow of the inhaled and/or exhaled air is measured by means of the flowmeter 105. These measurements are made continuously.

Figure 2:
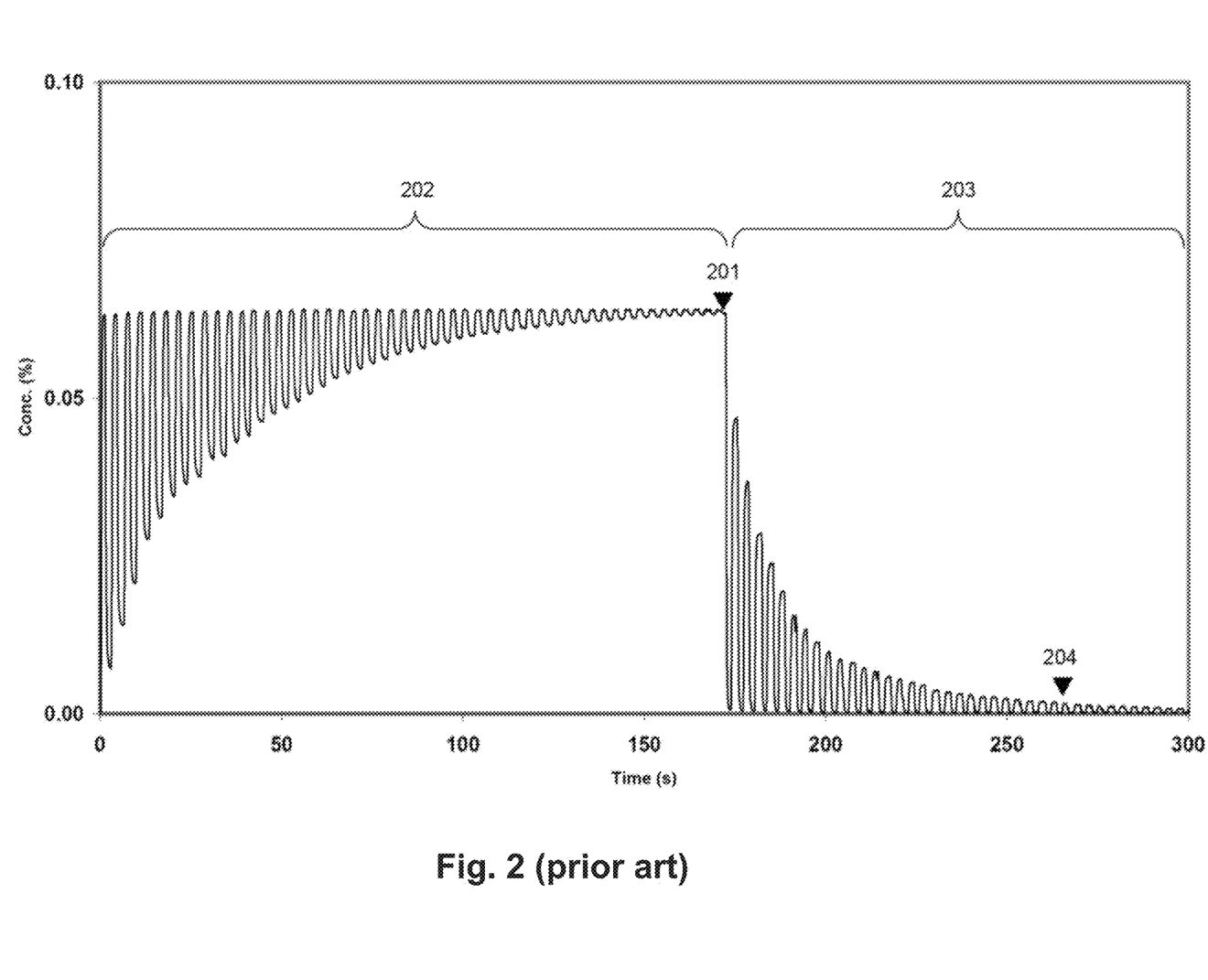
FIG. 2 (prior art) illustrates a curve from a conventional multi-breath wash-in/wash-out.

FIG. 2 (prior art) outlines a curve from a conventional multibreath wash-in/wash-out test from where LCI can be determined. The insoluble gas, $SF_6$, has become the gas of choice for measurement of LCI. The concentration of $SF_6$ is monitored and when the concentration is constant (below a predetermined threshold fluctuation) 201, the first time period called wash-in 202 is over. Hereafter the wash-out period 203 begins where the concentration of $SF_6$ is monitored until the concentration has reached 1/40 of the concentration in the beginning of the wash-out period 204. The cumulative expired volume ($V_{CE}$) required to clear the lungs of the gas down to 1/40 of its start concentration can then be used in combination with the functional residual capacity (FRC) to determine the LCI of the test subject. In the conventional MBW test the FRC is calculated from the net volume of inert gas exhaled divided by the difference in end-tidal concentration at the start and end of the wash-out:

$$FRC = \frac{\text{Net volume of inert gas exhaled}}{C_{ET,start} - C_{ET,end}}$$

As the net volume of inert gas exhaled (numerator) is obtained by integration of the product of respiratory flow and tracer gas concentration (i.e. expired and re-inspired tracer gas volumes on a breath-by-breath basis), accurate determination of the FRC requires a rapid dynamic response and data acquisition rate of the gas analyser. Proper alignment in time of the respiratory flow signal and tracer gas concentration prior to the calculation is also critical. This makes demands on the performance of the gas analyser and the calibration of the equipment.

Figure 3:
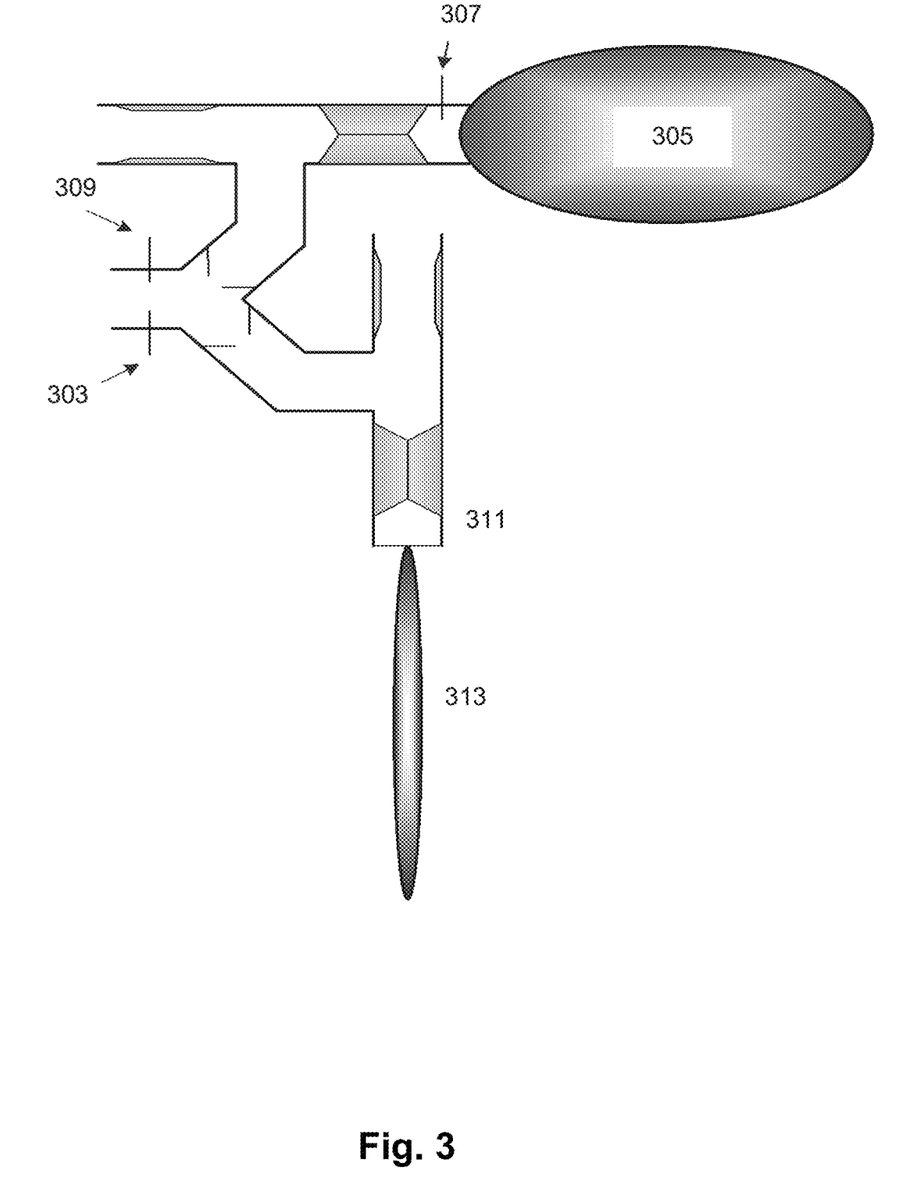
FIG. 3 is a schematic diagram illustrating one setup before starting the test for determination of FRC and ventilation distribution (LCI) as used in conjunction with the disclosed invention.

FIG. 3 is a schematic diagram illustrating one embodiment of the setup for determination of FRC and ventilation distribution (LCI) as used in conjunction with the disclosed invention. The setup in FIG. 3 shows the setup before the test is started. A breathing (inhalation) bag 305 is connected to the valve assembly 303 and is evacuated and pre-filled via a filling/evacuation line 307 with a gas mixture comprising the inert tracer gas. The control system is connected to the one way valve assembly via a gas sample line 309. The control system comprises a measuring apparatus comprising processing means and at least one gas analyser.

Figure 4:
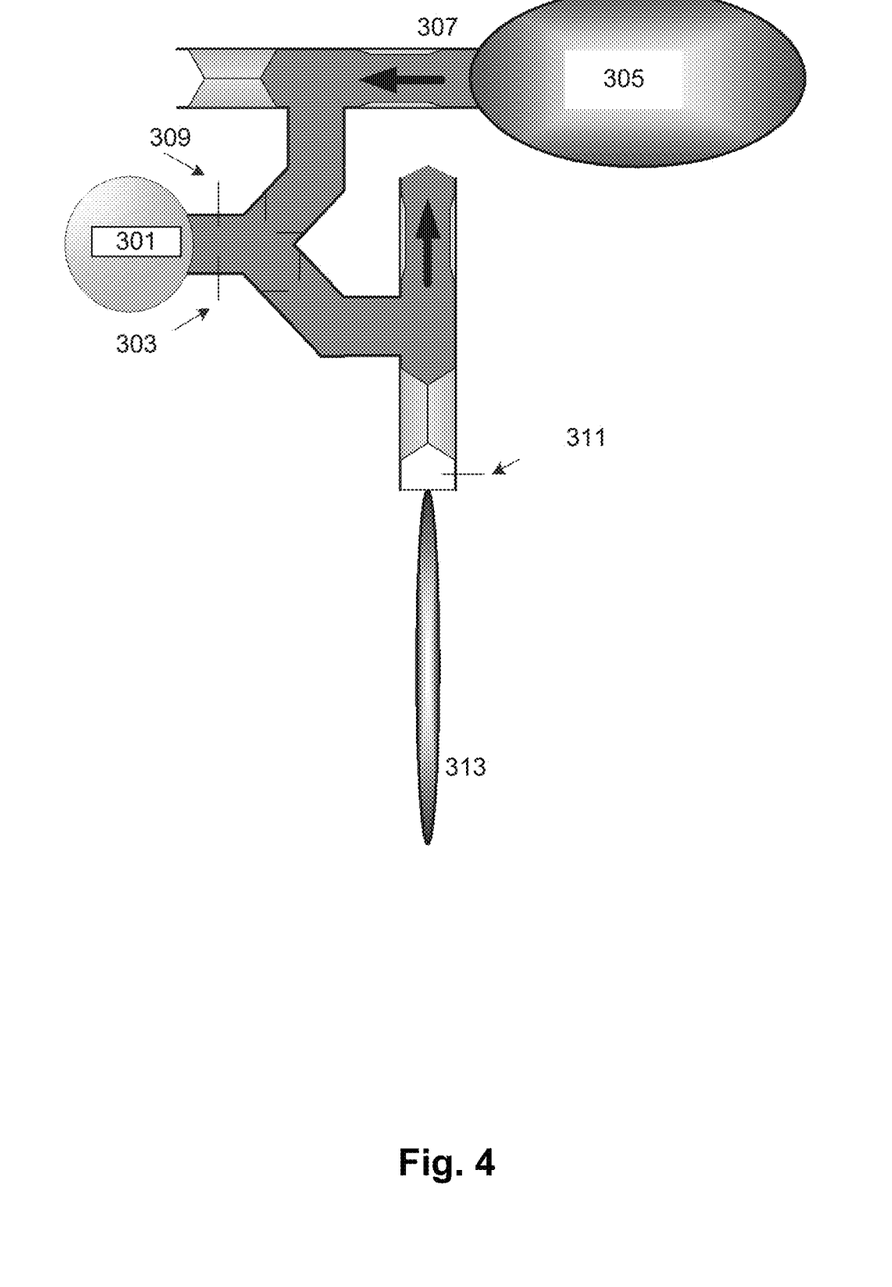
FIG. 4 is a schematic diagram illustrating an embodiment of the wash-in phase where the paediatric subject breathes in from the wash-in bag and out to room air.

FIG. 4 is shows an embodiment of the setup during wash-in. A test subject 301 having a facemask on or having the nose occluded with a nose clip breathes through the facemask or a mouthpiece, a bacterial filter and one port of the breathing valve assembly 303. The valve assembly 303 is a one way valve assembly comprising pneumatic valves that can open and close. A breathing (inhalation) bag pre-filled with inert tracer gas 305 is connected to the valve assembly and evacuated. The test subject 301 inhales the gas mixture comprising the inert tracer gas from the breathing bag 305 and exhales to the surroundings (see the arrows in the figure). The entry to the confined space (collection bag or washout bag) 313 via a filling/evacuation line 311 is closed by a valve during wash-in. During the wash-in the inert tracer gas concentration is measured to determine when the wash-in is complete (when the concentration is constant—below a predetermined threshold value regarding the fluctuation of the concentration). The pressure in the airways is also determined to determine the breathing phase of the test subject. The pressure is measured close to the mouth of the test subject (close to the end of the arrow of 303 in FIG. 4). The reason why the breathing phase of the test subject is important to know is that when $V_{CE}$ is calculated, dead space of the instruments are accounted for, which is why one need to know how many breaths (numbers) the test subject is having during the washout. The measure of the pressure in the airways to determine the breathing phase of the test subject is also important in order to be able to shift the valves in the assembly at the correct times during the test.

To perform the wash-in part of the test the valve assembly 303 is switched (e.g. automatically) to allow the test subject 301 to inspire from the bag 305 and exhale to the surroundings for a certain amount of time until the valve assembly 303 is switched to the next setup. The test subject 301 preferably uses a face mask instead of nose clip and mouthpiece. A typical test consists of a period where the test subject is inhaling the gas mixture from the breathing bag 305 and exhales to the surroundings (see the arrows in the figure) as explained above followed by a period where the test subject is inhaling fresh air from the surroundings and exhaling to the confined space (collection or washout bag) (see FIG. 5). During the testing (both during the wash-in and the wash-out period) the concentration in the inhaled and/or exhaled air of the inert gas in the mixture is measured by a fast responding gas analyser. Instead of gas concentration the gas analyser may equally well measure the partial pressure of the gas. The partial pressure can be obtained from the fractional concentration of dry gas or any other measure of gas concentration or pressure using appropriate conversion factors as known in the art.

Figure 8:
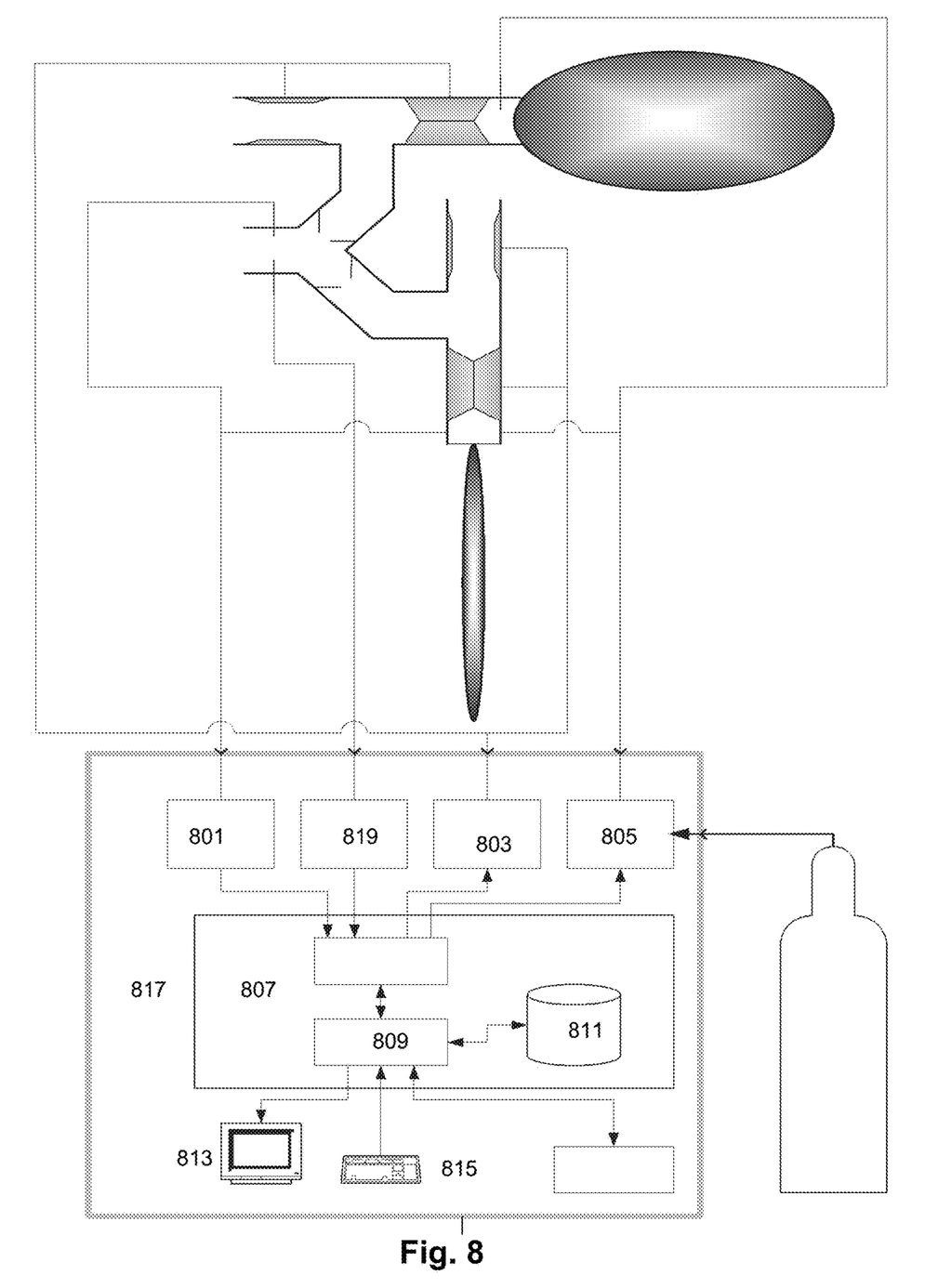
FIG. 8 shows the control system of the system.

The control system 817 (shown on FIG. 8) of the system comprises at least one gas analyser 801, a pressure monitoring unit 819 (unless the valve assembly is manually driven), a valve control unit 803 (unless the valve assembly is manually driven) and also a gas control unit 805 unless the inhalation bag 305 filled with the inert tracer gas is prepared manually. A control unit 807 can also be included, comprising a computing/processing unit (CPU) 809 with control interfaces, one or more program and data storage devices 811 and user interfaces for example comprising a display 813 and a keyboard 815, touch screen or similar input device. A data input/output module may also be included.

Figure 5:
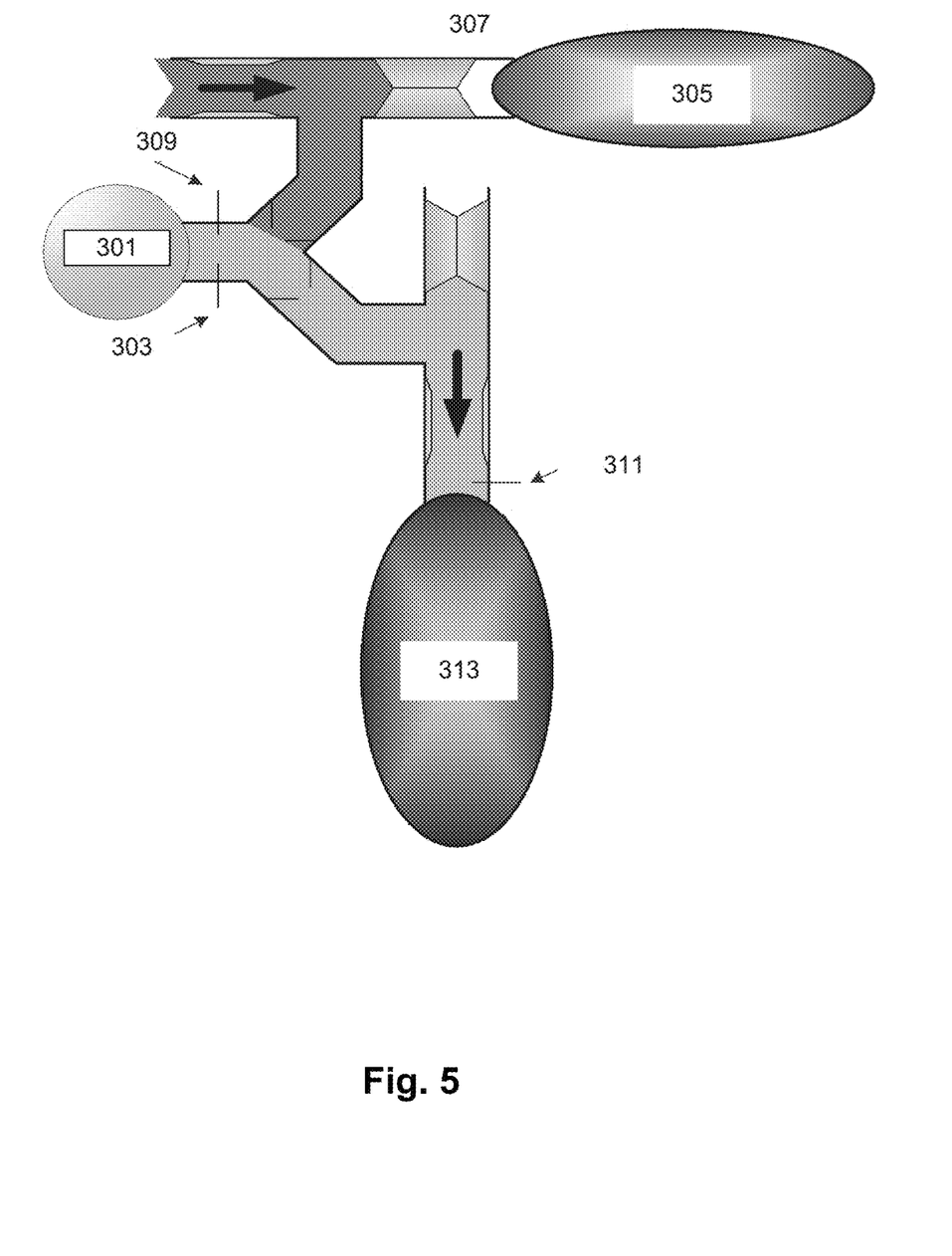
FIG. 5 is a schematic diagram illustrating an embodiment of the washout phase where the paediatric subject breathes in from room air and out into the confined space (here shown as a collection bag).

FIG. 5 is a schematic diagram illustrating an embodiment of the washout phase where the paediatric subject breathes in from room air (see arrows in FIG. 5) and out into the confined space (collection bag) 313. The tracer gas (e.g. $SF_6$) concentration is monitored at the end of each breath until the concentration has reached a predetermined concentration (e.g. 1/40) of the concentration in the beginning of the wash-out period and the expired gas is collected and measured to allow LCI calculation. The filling/evacuation line 307 is closed during washout by one of the valves in the valve assembly, whereas the filling/evacuation line 311 is open.

Since the test setup according to the invention does not need a flowmeter to determine the flow, it solves the issue of too large a dead space in the conventional MBW setup when it comes to testing paediatric subjects especially newborns and infants where the extra volume induced by the flowmeter will result in a very large dead space volume compared to the physiologic dead space.

Figure 6:
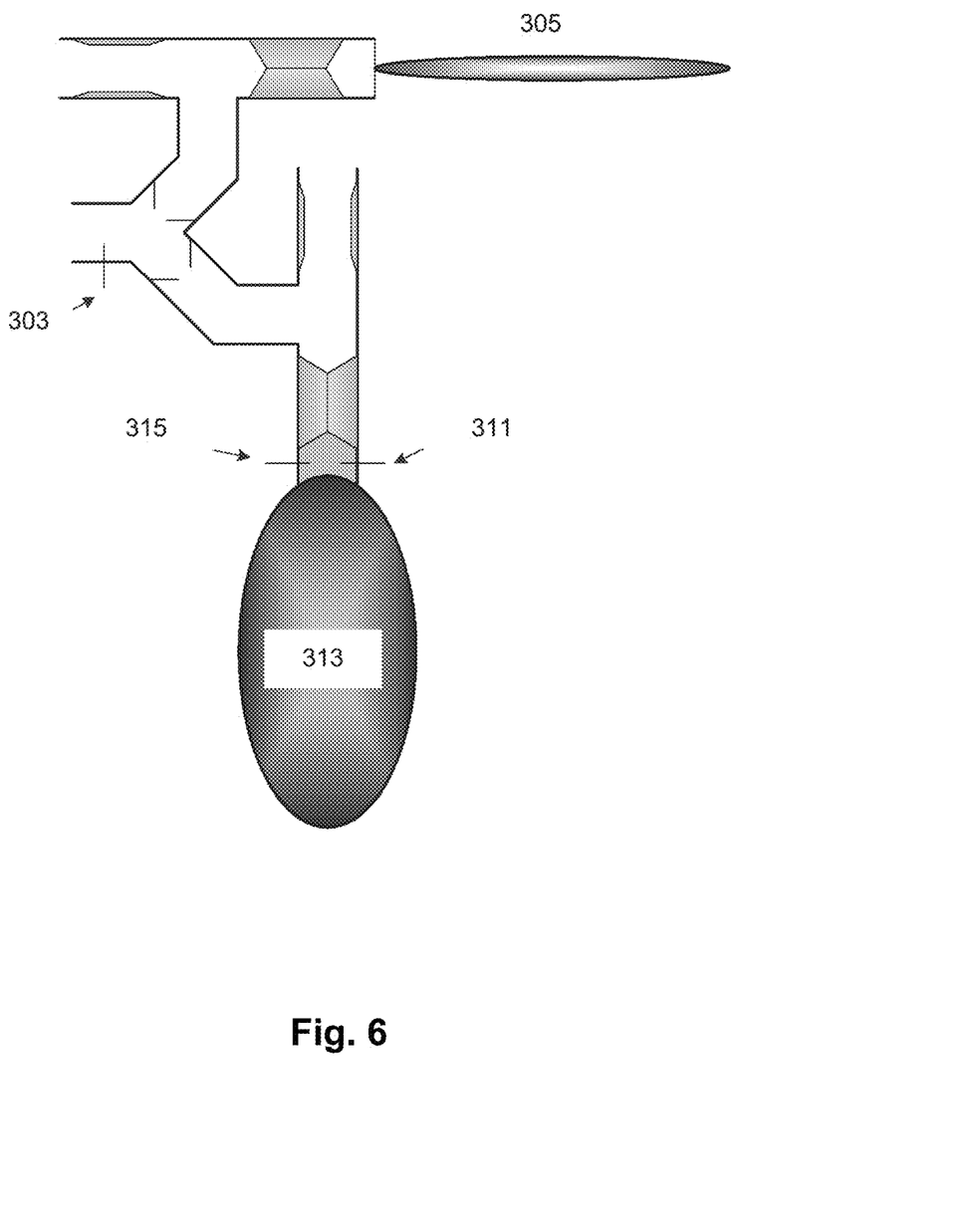
FIG. 6 is a schematic diagram illustrating an embodiment of the setup after the test is completed.

FIG. 6 is a schematic diagram illustrating an embodiment of the setup after the test is completed where the confined space (washout bag) is full of the inert tracer gas exhaled by the test subject. The control system is connected to the one way valve assembly via a gas sample line 315. The control system comprises a measuring apparatus comprising processing means and at least one gas analyser. The expired gas in the bag is measured to allow LCI calculation.

LCI represents the number of lung volume turnovers (i.e. FRCs) that the subject must breathe to clear the lungs from the tracer gas (by convention, to an end-tidal concentration of 1/40th of the starting concentration over three subsequent breaths). Disregarding the correction for external dead space the equation is:

$$LCI = \frac{V_{CE}}{FRC}$$

The concentration of the inert tracer gas is monitored and when the concentration is constant (below a predetermined threshold value regarding the fluctuation of the concentration), the first time period called wash-in is over. Hereafter the wash-out period begins where the concentration of the inert tracer gas is monitored at the end of each breath until the concentration has reached a predetermined (e.g. 1/40) of the concentration in the beginning of the wash-out period. It is not necessary to continuous monitor the instantaneous concentration during the whole breathing cycle since the net volume of inert tracer gas exhaled is determined by measuring the concentration of the inert tracer gas in the collection bag after completed wash-out and measuring the total volume in the collection bag after completed wash-out.

The net volume of inert tracer gas exhaled and the difference in end-tidal fractional concentration of the inert tracer gas at the start (in the below equation $SF6_{init}$) and end (in the below equation $SF6_{end}$) of the wash-out is used for accurate determination of the functional residual capacity (FRC) which is calculated according to the equation below:

$$FRC = \frac{SF6_{exp}}{SF6_{init} - SF6_{end}} \cdot V_{bag} \quad (ATPS)$$

Where $V_{bag}$ is calculated as below:

$$V_{bag} = T_{empty} \cdot Fill_{flow} \quad (ATPS)$$

And where $VCE = V_{bag}$ (ATPS)
Where
$T_{empty}$: Time to empty bag in seconds
$Fill_{flow}$: Calibrated filling flow (=emptying flow) in l/s
$SF6_{exp}$: Mean gas concentration of inert tracer gas in the collection bag
$SF6_{init}$: Gas concentration of inert tracer gas at the start of washout
$SF6_{end}$: End tidal gas concentration of inert tracer gas at the end of washout The multiple-breath wash-out (MBW) is used for determination of the cumulative expired volume ($V_{CE}$) required to clear the inert tracer gas from the lungs. $V_{CE}$ is determined by measuring the total volume in the collection bag after completed wash-out.

In the interest of brevity dead spaces on each side of the valve are not accounted for, but these can easily be incorporated.

In the below, are shown the equations when dead space are accounted for.

Formula for $V_{bag}$:

$$V_{bag} = T_{empty} \cdot (Fill_{flow} + 0.120/60) + (T_{stop} - T_{start}) \cdot 0.5 \cdot 0.120/60 \quad (ATPS)$$

Where
$T_{empty}$: Time to empty bag in seconds
$Fill_{flow}$: Calibrated filling flow (=emptying flow) in l/s
0.120/60: The gas sample flow is assume to be 120 ml/min and is evacuating the bag at the same time as the evacuation pump.
$(T_{stop} - T_{start})$: Washout time in seconds. During expiration in the washout period, the gas sample flow is reducing the amount of air going to the bag. It is assumed that $T_{insp} = T_{exp}$, so only during 0.5 of time the gas sample flow is added.

Formula for FRC: When wash-in is completed all dead spaces and lung volume are equilibrated to $SF6_{init}$:

$$SF6\_volume(0) = SF6_{init} \cdot (FRC + V_{Inst.DS,0} + V_{Inst.DS,1} + V_{Inst.DS,2}) \quad (ATPS)$$

$V_{Inst\_DS,0}$ is the wash-in valve dead space which is in the order of 12 ml such as between 10 14 ml. $V_{Inst\_DS,1}$ is the mouth piece dead space which is in the order of 4 ml (+bacterial dead space) such as in the order of 3 to 5 ml and $V_{Inst\_DS,2}$ is the washout valve dead space which is in the order of 12 ml such as between 10 14 ml. When wash-out is completed the lung volume and dead space 1 and 2 are filled with 1/40 of the $SF6_{init}$ and the rest is collected in the bag:

$$SF6\_volume(1) = V_{bag} \cdot SF6_{exp} + 0.025 \cdot SF6_{init} \cdot (FRC + V_{Inst.DS,1} + V_{Inst.DS,2}) \quad (ATPS)$$

The above 2 volumes of $SF_6$ are equal, i.e.:

$$SF6_{init} \cdot (FRC + V_{Inst.DS,0} + V_{Inst.DS,1} + V_{Inst.DS,2}) \\ = V_{bag} \cdot SF6_{exp} + 0.025 \cdot SF6_{init} \cdot (FRC + V_{Inst.DS,1} + V_{Inst.DS,2}) \quad (ATPS)$$

Rearranging them gives the formula for FRC:

$$FRC = \frac{SF6_{exp}}{SF6_{init} - 0.975} \cdot V_{bag} - \frac{1}{0.975} \cdot V_{Inst.DS,0} - V_{Inst.DS,1} - V_{Inst.DS,2} \quad (ATPS)$$

Formula for VCE: $V_{bag}$ is the total expired volume during the washout and in order to correct for instrument dead space the term $N_{breath} \cdot V_{InstDS,1}$ is subtracted.

$$VCE = V_{bag} - N_{breath} \cdot V_{Inst.DS,1} \quad (ATPS)$$

LCI is then determined as:

$$LCI = VCE/FRC$$

The gas dilution technique according to the present invention is more robust than the traditional wash-out technique for determination of FRC, because it is independent of the critical time alignment between gas analyser and flowmeter signals. Further, it relaxes the requirements to rise time of the gas analyser because only end-tidal concentrations are needed in determining the gas dilution, whereas in the conventional open-circuit method a short rise time and accurate time alignment prior to integrating the product of flow and gas concentration signals are important in order to obtain accurate values of the flux of $SF_6$ in the rapid transitions during the beginning of expiration (phase II of the breath) and inspiration.

Figure 7:
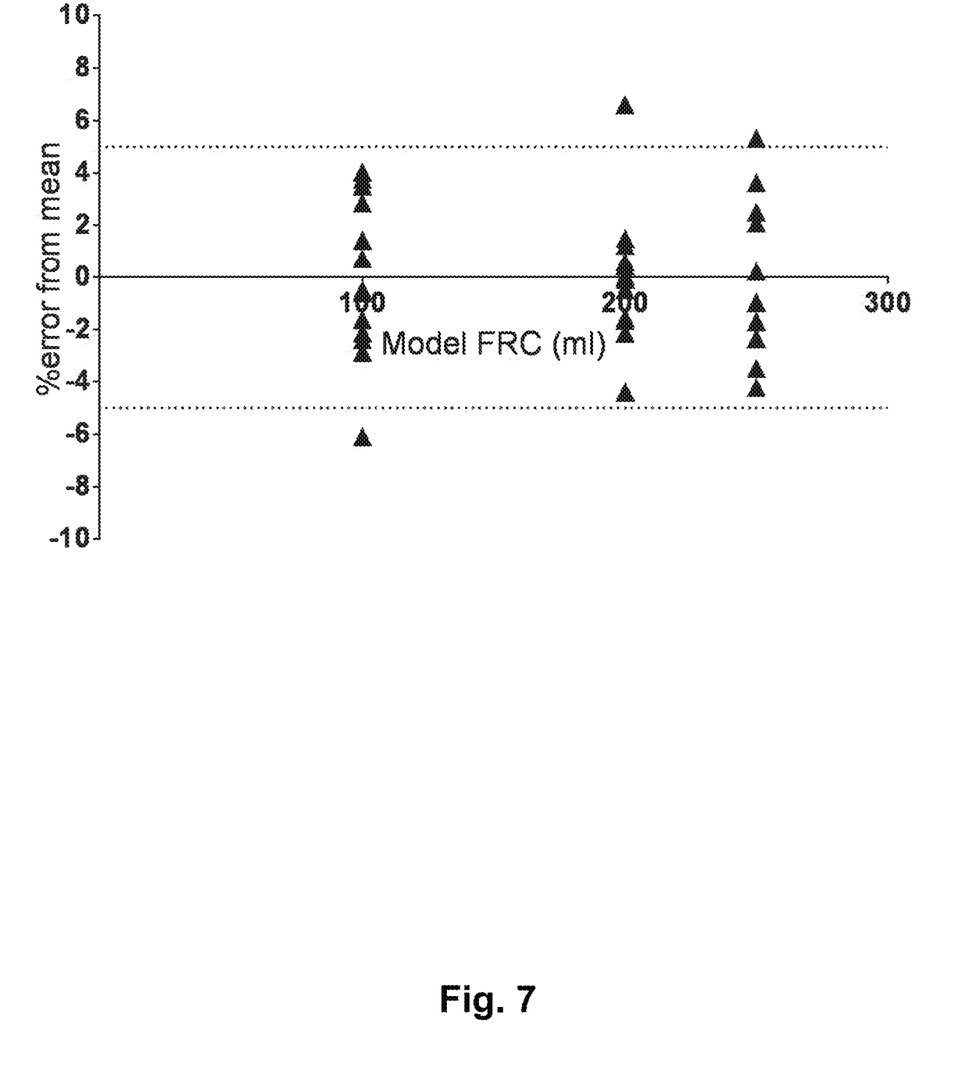
FIG. 7 shows the results from a model lung.

FIG. 7 shows the results from a model lung. A prototype paediatric MBW system was assessed in vitro using a lung model based on a mechanically driven 100 ml syringe and ventilation tank. A 100 ml calibrated syringe is driven by a linear motor, the syringe movement distance (equivalent to tidal volume) and rate are set by a computer. The model was set to deliver FRC's of 100 ml-250 ml, with corresponding tidal volumes of 30-90 mls and respiratory rates of 20-60 $min^{-1}$. Improvements to hardware and wash-in protocol were made following initial testing. This offers improved accuracy at small volumes and fast respiratory rates, compared to previously described lung models which have used a portable ventilator. The lung tank consists of two separate compartments of known volume, filled with water to a set level to determine FRC. The lung tank is then heated and humidified to BTPS conditions by placing in an external tank containing hot water. Temperature is monitored and kept constant throughout at 36.5-37.3 degrees. The system was initially tested in an unheated lung model. Overall error of FRC measurement was 0.04%, and only one of 21 repeat FRC measurements was outside the +/−5% error range (see the below table). Testing was repeated in the lung model heated to BTPS conditions. Over 36 tests, overall error of FRC measurement was 0.0006%. The results are illustrated in FIG. 7 which shows the percentage error from the overall mean of each measurement at FRCs of 100 ml, 200 ml and 250 ml at BTPS conditions. The dotted lines indicate the 95% accuracy target range.

| Model FRC (ml) (inc deadspace) | Measured FRC (ml) | 95% CI measured FRC (ml) | Mean (SD) % error |
| --- | --- | --- | --- |
| 102 | 99.2 | 97.0-101.5 | −1.76 (1.8) |
| 202 | 203.3 | 199.4-207.3 | 1.17 (2.34) |
| 252 | 250.6 | 247.4-253.8 | −0.18 (1.63) |

It should be noted that the above-mentioned means of implementation illustrate rather than limit the invention, and that those skilled in the art will be able to suggest many alternative means of implementation without departing from the scope of the appended claims. Rather, the words used in the specification are words of description rather than limitation, and it is understood that various changes may be made without departing from the scope of the invention. The word 'comprising' does not exclude the presence of other elements or steps than those listed in a claim. The invention can be implemented by means of hardware and software comprising several distinct elements, and by means of a suitably programmed computer. In a device claim enumerating several means, several of these means can be implemented by one and the same item of hardware or software. The mere fact that certain measures are recited in mutually different dependent claims does not indicate that a combination of these measures cannot be used to advantage.

The invention claimed is:

1. A method to determine a lung clearance index (LCI) of a paediatric test subject, the method comprising:
   wash-in of an inert tracer gas until a constant concentration of the inert tracer gas in lungs of a paediatric test subject is reached, the wash-in is conducted using open circuit wash-in comprising a non-rebreathing valve assembly constructed by one-way valves, where the paediatric test subject inhales the inert tracer gas from an inhalation bag to wash-in the inert tracer gas while expiring into room air;
   measuring an end-tidal fractional concentration of the inert tracer gas at a beginning of a wash-out period;
   wash-out of the inert tracer gas from the lungs of the paediatric test subject during a wash-out period until an end-tidal tracer gas concentration has fallen below a predetermined fraction of the concentration in the beginning of the wash-out period, wherein the wash-out is conducted by inhaling atmospheric air from surroundings and exhaling to a collection bag collecting aspirate;
   measuring an end-tidal fractional concentration of the inert tracer gas at an end of the wash-out period;
   measuring the concentration of the inert tracer gas in the collection bag after the wash-out period; and
   measuring a volume of the collection bag after the wash-out period to obtain a total cumulative expired volume (VCE);
   wherein
   the lung clearance index (LCI) is determined by:
      determining a net volume of inert tracer gas exhaled by the paediatric test subject based on the concentration of the inert tracer gas in the collection bag after completed wash-out period and the total cumulative expired volume (VCE);
      determining a functional residual capacity (FRC) by dividing the net volume of inert tracer gas exhaled by the paediatric test subject with a difference in end-tidal fractional concentrations of the inert tracer gas at the start and at the end of the wash-out period; and
      calculation of the LCI as a ratio between VCE and FRC, wherein during the method there is no determination of flow of air inhaled and/or exhaled by the paediatric test subject.

2. The method according to claim 1, wherein the inert tracer gas is a gas with a negligible solubility in blood and tissue.

3. The method according to claim 1, wherein the inert tracer gas is SF6.

4. The method according to claim 1, wherein the inert tracer gas is comprised in an oxygen enriched gas mixture.

5. The method according to claim 1, wherein determination of the gas concentration is performed by a mass spectrometer or at least one sensitive gas analyser.

6. The method according to claim 5, wherein the determination of the gas concentration is based on photoacoustic spectroscopy (PAS).

7. A system adapted to determine a lung clearance index (LCI) of lungs of a paediatric test subject, the system comprising;
   a valve assembly setup comprising:
      an inhaler device for the paediatric test subject to inhale an inert tracer gas mixture comprising an inert tracer gas in an open circuit wash-in, the inhaler device comprising a non-rebreathing valve assembly constructed by one-way valves, where the paediatric test subject inhales the inert tracer gas from an inhalation bag to wash-in the inert tracer gas while expiring into room air;
   a collection bag for the paediatric test subject to exhale to for collection of an exhaled volume of gas by the paediatric test subject during a wash-out period, the volume comprising the inert tracer gas;
   at least one gas analyser for obtaining a fractional concentration at an end of each breath of the inert tracer gas inhaled and exhaled by the paediatric test subject until the concentration has reached a predetermined fraction of the concentration in a beginning of the wash-out period;

processing means for determining the LCI of the lungs of the paediatric test subject by:

using a net volume of inert tracer gas exhaled by the paediatric test subject during the wash-out period, the net volume of inert tracer gas exhaled is obtained by measuring the concentration of the inert tracer gas in the collection bag after completed wash-out period and measuring a total cumulative expired volume (VCE) in the collection bag after completed wash-out period, where the total cumulative expired volume (VCE) is the volume required to clear an inert tracer gas concentration from the lungs of the paediatric test subject below the predetermined fraction of the concentration in the beginning of the wash-out period;

determining a functional residual capacity (FRC) by dividing the net volume of inert tracer gas exhaled by the paediatric test subject during the wash-out period with a difference in end-tidal fractional concentration of the inert tracer gas at a start and an end of the wash-out period;

where LCI is determined as a ratio between VCE and FRC, wherein the system does not comprise a flow meter that determines flow of air inhaled and/or exhaled by the paediatric test subject.

8. The system according to claim 7, wherein the inhalation bag is prefilled with the inert tracer gas mixture comprising the inert tracer gas.

9. The system according to claim 7, wherein the inert tracer gas is a gas with a negligible solubility in blood and tissue.

10. The system according to claim 7, wherein the inert tracer gas is SF6.

11. The system according to claim 7, wherein the inert tracer gas is comprised in an oxygen enriched gas mixture.

12. The system according to claim 7, wherein the at least one gas analyser is a mass spectrometer or a sensitive gas analyser.

13. The system according to claim 12, wherein the at least one gas analyser is based on PAS.

14. The system according to claim 7 comprising a cylinder for containing the inert tracer gas mixture and a dilution device to dilute the inert tracer gas mixture with air or oxygen.

15. The system according to claim 7, wherein the at least one gas analyser for obtaining the fractional concentration of the inert tracer gas inhaled and exhaled by the test subject comprises means for obtaining the partial pressure of the inert tracer gas.

16. A non-transitory computer-readable medium having stored therein instructions for causing a processing unit to execute the processes of:

determining when a constant concentration of an inert tracer gas in lungs of a paediatric test subject has been reached during wash-in of the inert tracer gas;

measuring an end-tidal fractional concentration of the inert tracer gas at a beginning of a wash-out period, wherein the inert tracer gas is directed to a collection bag during the wash-out period;

determining when an end-tidal tracer gas concentration has fallen below a predetermined fraction of the concentration in the beginning of the wash-out period;

measuring an end-tidal fractional concentration of the inert tracer gas at an end of the wash-out period;

measuring the concentration of the inert tracer gas in the collection bag after the wash-out period; and measuring a volume of the collection bag after the wash-out period to obtain a total cumulative expired volume (VCE);

wherein the lung clearance index (LCI) is determined by:

determining a net volume of inert tracer gas exhaled by the paediatric test subject based on the concentration of the inert tracer gas in the collection bag after completed wash-out period and the total cumulative expired volume (VCE);

determining a functional residual capacity (FRC) by dividing the net volume of inert tracer gas exhaled by the paediatric test subject with a difference in end-tidal fractional concentrations of the inert tracer gas at the start and at the end of the wash-out period; and calculation of the LCI as a ratio between VCE and FRC, wherein the non-transitory computer-readable medium does not have instructions stored therein for causing a processing unit to execute the process of determining flow of air inhaled and/or exhaled by the paediatric test subject.

* * * * *